(12) United States Patent
Phull et al.

(10) Patent No.: US 8,519,126 B2
(45) Date of Patent: Aug. 27, 2013

(54) CRYSTALLINE FORM OF TENOFOVIR DISOPROXIL AND A PROCESS FOR ITS PREPARATION

(75) Inventors: Manjinder Singh Phull, Maharashtra (IN); Rajendra Narayanrao Kankan, Maharashtra (IN); Dharmaraj Ramachandra Rao, Maharashtra (IN)

(73) Assignee: Cipla Limited, Mumbai (IN)

( * ) Notice: Subject to any disclaimer, the term of this patent is extended or adjusted under 35 U.S.C. 154(b) by 280 days.

(21) Appl. No.: 12/989,147

(22) PCT Filed: Jul. 30, 2008

(86) PCT No.: PCT/GB2008/002619
§ 371 (c)(1),
(2), (4) Date: Jan. 5, 2011

(87) PCT Pub. No.: WO2009/130437
PCT Pub. Date: Oct. 29, 2009

(65) Prior Publication Data
US 2011/0112292 A1   May 12, 2011

(30) Foreign Application Priority Data
Apr. 25, 2008   (IN) .......................... 917/MUM/2008

(51) Int. Cl.
*C07F 9/02* (2006.01)
(52) U.S. Cl.
USPC ........................................................ 544/244
(58) Field of Classification Search
USPC ........................................................ 544/244
See application file for complete search history.

(56) References Cited

U.S. PATENT DOCUMENTS

| 5,733,788 A | 3/1998 | Bischofberger |
| 5,922,695 A | 7/1999 | Arimilli et al. |
| 5,935,946 A | 8/1999 | Munger, Jr. et al. |
| 5,977,089 A | 11/1999 | Arimilli et al. |
| 6,465,649 B1 | 10/2002 | Gutierrez et al. |
| 2004/0018150 A1 | 1/2004 | Becker et al. |
| 2009/0012292 A1* | 1/2009 | Parthasaradhi Reddy et al. ............... 544/244 |
| 2011/0009368 A1* | 1/2011 | Dova .............................. 514/81 |

FOREIGN PATENT DOCUMENTS

| WO | WO 2007013085 A1 * | 2/2007 |
| WO | 2008007392 A2 | 1/2008 |
| WO | 2009130437 A1 | 10/2009 |

OTHER PUBLICATIONS

Arimilli, MN et al. (1997) "Synthesis, in vitro biological evaluation and oral bioavailability of 9-[2-(phosphonomethoxy)propyl]adenine (PMPA) prodrugs", Antiviral Chemistry & Chemotherapy, vol. 6(6), p. 557-564.*
Foreign communication from the priority application—International Preliminary Report on Patentability, PCT/GB2008/002619, Oct. 26, 2010, 9 pages.
Foreign communication from the priority application—International Search Report and Written Opinion, PCT/GB2008/002619, May 15, 2009, 17 pages.

* cited by examiner

*Primary Examiner* — Noble Jarrell
*Assistant Examiner* — Laura Daniel
(74) *Attorney, Agent, or Firm* — Conley Rose, P.C.; Rodney B. Carroll

(57) ABSTRACT

Crystalline Form C of tenofovir disoproxil, salts thereof and a process for its preparation. The process involves adding a solution comprising tenofovir disoproxil and an organic solvent to salt-saturated water, whereby the crystalline Form C of tenofovir disoproxil precipitates. The crystalline Form C of tenofovir disoproxil may be converted to a salt thereof. There is also provided a process for purifying a crude product comprising tenofovir monoisoproxil and tenofovir disoproxil.

18 Claims, 2 Drawing Sheets

CRYSTALLINE FORM OF TENOFOVIR DISOPROXIL AND A PROCESS FOR ITS PREPARATION

CROSS-REFERENCE TO RELATED APPLICATIONS

This application is a filing under 35 U.S.C. 371 of International Application No. PCT/GB2008/002619 filed Jul. 30, 2008, entitled "Crystalline Form of Tenofovir Disoproxil and a Process for its Preparation," claiming priority of Indian Patent Application No. 917/MUM/2008 filed Apr. 25, 2008, which applications are incorporated by reference herein in their entirety.

BACKGROUND OF THE INVENTION

Tenofovir disoproxil fumarate (TDF, formerly known as bis(POC)-PMPA) is a bis-ester prodrug of the acyclic nucleoside phosphonate tenofovir.

Tenofovir disoproxil fumarate is as an orally-active form of tenofovir. Tenofovir which is chemically named as 9-[2-(R)-(Phosphonomethoxy)propyl]adenine, (PMPA), (I) has a strong activity against human immunodeficiency virus infection in humans.

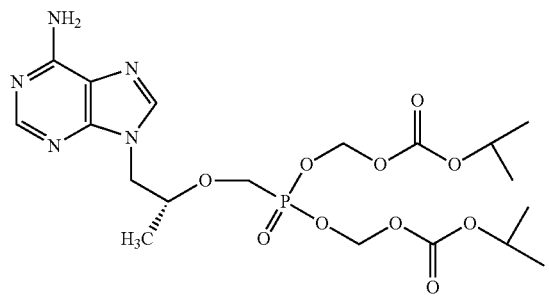

(I)

U.S. Pat. No. 5,733,788 describes a process for the synthesis of PMPA wherein (R)-9-[2-(hydroxyl)propyl]adenine is condensed with diethyl p-toluenesulfonyoxy methylphosphonate in the presence of lithium hydride followed by dealkylation to give tenofovir disoproxil.

U.S. Pat. No. 5,922,695 describes a process for the synthesis of PMPA wherein the condensation is carried out using lithium tert-butoxide. It is further disclosed that tenofovir disoproxil base is obtained as an oil which is converted to its fumarate salt.

Several patents such as US 2004/0018150, U.S. Pat. Nos. 6,465,649, 5,935,946, 5,977,089 disclose various processes for the synthesis of tenofovir disoproxil and its salts. In all of these processes, tenofovir disoproxil base is either described as an oil or is converted to its fumarate salt without isolating the base.

WO 2008/007392 describes tenofovir disoproxil base as a crystalline solid. The crystalline base is characterized by IR, XRD and DSC and is isolated from the reaction mass after being subjected to multiple steps of purification and crystallization. Finally, crystalline tenofovir disoproxil base is isolated from an organic solvent.

Tenofovir disoproxil is a very important candidate for the treatment against HIV virus, as is evident from the literature which describes various attempts to provide alternate methods for the synthesis of this drug for the benefit of society. The present invention is one such attempt in providing a simple and eco-friendly process for the isolation of tenofovir disoproxil base.

OBJECT OF THE INVENTION

The object of the present invention is to provide a simple process for the isolation of crystalline tenofovir disoproxil base.

Another object of the present invention is to provide an eco-friendly process which avoids the use of any organic solvent for the isolation of crystalline tenofovir disoproxil.

Yet another object of the present invention is to provide a crystalline tenofovir disoproxil Form C which is substantially free of impurities.

SUMMARY OF THE INVENTION

According to a first aspect of the present invention, there is provided crystalline Form C of tenofovir disoproxil.

In an embodiment, crystalline Form C of tenofovir disoproxil is characterised as having an XRPD pattern comprising peaks at 6.8, 23.2, 25.5 and 31.7°2θ±0.2°2θ. Typically, the XRPD pattern comprises further peaks at 8.3, 17.4, 18.7 and 22.9°2θ±0.2°2θ.

In an embodiment, crystalline Form C of tenofovir disoproxil is characterised as having an XRPD pattern with peaks as shown in Table 1 below.

In an embodiment, crystalline Form C of tenofovir disoproxil is characterised as having an XRPD pattern as shown in FIG. 1.

Crystalline Form C of tenofovir disoproxil may be having a melting point ranging from 61° C. to 66° C. Typically, crystalline Form C of tenofovir disoproxil is characterised as having a DSC pattern as shown in FIG. 2.

In an embodiment, crystalline Form C of tenofovir disoproxil contains less than 0.2% tenofovir monoisoproxil, typically as measured by HPLC.

According to another aspect of the present invention, there is provided a process for preparing crystalline Form C of tenofovir disoproxil or a salt thereof, the process comprising adding a solution comprising tenofovir disoproxil and an organic solvent to salt-saturated water, whereby the crystalline Form C of tenofovir disoproxil precipitates, and optionally converting the crystalline Form C of tenofovir disoproxil to a salt of crystalline Form C of tenofovir disoproxil. Suitably, the crystalline Form C of tenofovir disoproxil as prepared by the process is as described above.

In an embodiment, no organic solvents, other than the organic solvent in which the tenofovir disoproxil is dissolved, are used. This is particularly advantageous as the process is eco-friendly for not using additional organic solvents.

In an embodiment, the salt-saturated water is water saturated with an alkali or alkaline earth metal salt. Suitably, the salt-saturated water is water saturated with sodium chloride.

The organic solvent is suitably a water miscible organic solvent such as N-methyl pyrrolidone or dimethyl sulfoxide. Suitably, the organic solvent is N-methylpyrrolidone.

Advantageously, the aqueous solution comprising the tenofovir disoproxil is cooled to a temperature below 0° C. Suitably, the temperature ranges from −20° C. to 0° C. Preferably, the temperature ranges from −20° C. to −10° C. Suitably, the temperature ranges from −20° C. to −15° C.

The crystalline Form C of tenofovir disoproxil may be converted to a salt thereof. For example, the salt may be the fumarate salt of crystalline Form C. Any typical reagents and conditions for preparing the fumarate salt may be used for the conversion, for example, those disclosed in WO 2008/007392.

The process for preparing crystalline Form C is effective in removing impurities present in the tenofovir disoproxil starting material. More particularly it helps in removing the monoisoproxil impurity. Form C product can be further purified by formation of the salt, for example, the fumarate salt, to result in a product having high purity.

In an embodiment, the solution of the tenofovir disoproxil in the organic solvent is the reaction mass resulting from a synthesis of the tenofovir disoproxil. In other words, tenofovir disoproxil may be prepared and the reaction mass used directly in the process of the present invention for preparing Form C of tenofovir disoproxil. For example, the tenofovir disoproxil may be prepared by condensing 9-[2-(R)-(phosphonomethoxy)propyl]adenine (PMPA) with chloromethyl isopropyl carbonate in the organic solvent and in the presence of a base such as triethyl amine. In an alternative embodiment, the solution of tenofovir disoproxil is prepared by dissolving crude tenofovir disoproxil or any crystalline form of tenofovir disoproxil in the organic solvent.

During the reaction of PMPA and chloromethyl isopropyl carbonate, the impurity tenofovir monisoproxil is formed to an extent of 15-20%. Upon formation of Form C of tenofovir disoproxil using the saturated salt solution according to the present invention, the monoisoproxil impurity is removed such that it is present in an amount of less than 1%, preferably less than 0.5%, more preferably less than 0.2%. If the Form C is further converted to a salt, such as the fumarate salt, the amount of monoisoproxil may be further reduced to result in a highly-pure salt of tenofovir disoproxil.

Thus, the process of the present invention for preparing crystalline Form C of tenofovir disoproxil may be seen as a process for purifying crude tenofovir disoproxil.

The precipitated Form C of tenofovir disoproxil may be isolated or it may be used directly in the preparation of the salt thereof. Suitable isolation techniques are well known to those skilled in the art and include filtration followed by drying.

Crystalline Form C of tenofovir disoproxil prepared according to the process described above forms another aspect of the present invention.

According to another aspect of the present invention, there is provided a process for purifying a crude product comprising tenofovir disoproxil and tenofovir monoisoproxil, the process comprising i) dissolving the crude product in a water immiscible solvent; ii) washing the solution of the crude product with salt-saturated water; and iii) isolating a purified product comprising tenofovir disoproxil and a reduced amount of tenofovir monoisoproxil.

Tenofovir monoisoproxil is an impurity and it is a major advantage to provide a simple and efficient process for reducing the amount of tenofovir monoisoproxil in a crude product. By using the purification process of the present invention, the amount of tenofovir monoisoproxil in the purified product is reduced relative to the amount of tenofovir monoisoproxil in the crude product. The purified product is substantially free of monoisoproxil impurity and is isolated by removal of the solvent. The amount of tenofovir monoisoproxil in the purified product is reduced to a level of less than 1% preferably below 0.2%. The term "substantially free of" means less than 1%, preferably less than 0.2%. The purified product may be in the polymorphic Form C as described above. Alternatively, the purified product may be in any polymorphic form.

Addition of the salt-saturated solution to the solution of the crude product results in the formation of an organic layer and an aqueous layer. The organic layer may be washed several times, for example 2 or 3 times, with salt-saturated water, then separated from the aqueous layer and the solvent removed to isolate the purified product.

The water immiscible solvent may be ethyl acetate, isopropyl acetate, toluene, methyl isobutyl ketone, ethylene dichloride or methylene dichloride, preferably the solvent is methylene dichloride.

In an embodiment, the salt-saturated water is water saturated with an alkali or alkaline earth metal salt. Suitably, the salt-saturated water is water saturated with sodium chloride.

The purified tenofovir disoproxil may be converted to a salt of tenofovir disoproxil. The salt may be the fumarate salt. Any typical reagents and conditions for preparing the fumarate salt may be used for the conversion, for example, those disclosed in WO 2008/007392.

The process removes the monoisoproxil impurity such that it is present in the final product in an amount less than 1%, preferably less than 0.5%, typically less than 0.2%. The product can be further purified by formation of the salt, for example the fumarate salt, to result in a product having very high purity.

In an embodiment, the crude product comprising the tenofovir monoisoproxil and disoproxil is the reaction mass resulting from a synthesis of the tenofovir disoproxil. In other words, tenofovir disoproxil may be prepared and the reaction mass used directly in the process of the present invention for removing tenofovir monoisoproxil. For example, the tenofovir disoproxil may be prepared by condensing 9-[2-(R)-(phosphonomethoxy)propyl]adenine (PMPA) with chloromethyl isopropyl carbonate in the organic solvent and in the presence of a base such as triethyl amine. In an alternative embodiment, the solution of tenofovir disoproxil is prepared by dissolving crude tenofovir disoproxil or any crystalline form of tenofovir disoproxil in the organic solvent.

During the reaction of PMPA and chloromethyl isopropyl carbonate, the impurity tenofovir monisoproxil is formed to an extent of 15-20%. Using the removal process of the present invention, the monoisoproxil impurity is removed such that it is present in an amount of less than 1%, preferably less than 0.5%, more preferably less than 0.2%. If the product is further converted to a salt, such as the fumarate salt, the amount of monoisoproxil may be further reduced to result in a highly-pure salt of tenofovir disoproxil.

The purified tenofovir disoproxil may be used directly in the preparation of the salt thereof. Suitable isolation techniques are well known to those skilled in the art and include filtration followed by drying.

The fumarate salt of tenofovir disoproxil prepared according to the processes described above forms another aspect of the present invention.

According to another aspect of the present invention, there is provided a pharmaceutical composition comprising tenofovir disoproxil fumarate of the present invention and one or more pharmaceutically acceptable excipients.

The pharmaceutically acceptable excipients to be used in the pharmaceutical composition of the present invention are well known to those skilled in the art.

According to another aspect of the present invention, there is provided tenofovir disoproxil fumarate of the present invention for use in medicine.

According to another aspect of the present invention, there is provided tenofovir disoproxil fumarate of the present invention for use in treating HIV.

According to another aspect of the present invention, there is provided the use of tenofovir disoproxil fumarate of the present invention for use in the manufacture of a medicament for treating HIV.

According to another aspect of the present invention, there is provided a method of treating HIV comprising administering to a patient in need thereof tenofovir disoproxil fumarate of the present invention.

DETAILED DESCRIPTION OF THE INVENTION

In one aspect, the present invention provides a simple and eco-friendly process for the isolation of tenofovir disoproxil from the reaction mass using water.

Tenofovir disoproxil may be synthesized by condensing 9-[2-(R)-(phosphonomethoxy)propyl]adenine with chloromethyl isopropyl carbonate in a water miscible organic solvent, preferably N-methylpyrrolidone, in the presence of triethyl amine. After reaction completion, the reaction mass is quenched in water saturated with alkali or alkaline earth metal salts, preferably in water saturated with sodium chloride, and the saturated aqueous solution is chilled to a temperature below 0 to −20° C. preferably below −15° C. more preferably below −10° C.

It is not possible to isolate tenofovir disoproxil base in solid form by simply quenching the reaction mass in water: by doing so it forms an oil and does not convert to a solid unless it is further purified and isolated from an organic solvent.

In the process of the present invention, the reaction mass is quenched slowly in salt-saturated water at a temperature below 0° C. These parameters assist in providing a metastable zone which facilitates the precipitation of tenofovir disoproxil as a crystalline solid.

The process of the present invention avoids the use of organic solvents for the isolation of tenofovir disoproxil; instead crystalline tenofovir disoproxil base is isolated from water.

In the process of the present invention, the major impurities formed in the reaction, particularly tenofovir monoisoproxil, are efficiently removed by the use of saturated water which also assists in precipitating tenofovir disoproxil base in a crystalline form.

The crystalline solid obtained by the process of the present invention hereinafter is termed as tenofovir disoproxil Form C. In an embodiment, tenofovir disoproxil Form C is substantially free of the monoisoproxil impurity. Preferably, the monoisoproxil impurity is present in an amount less than 1%, more preferably less than 0.2% by HPLC. Tenofovir disoproxil base Form C of the present invention is characterized by XRD and DSC.

In yet another aspect, crystalline tenofovir disoproxil Form C may also be prepared by dissolving crude tenofovir disoproxil base or any crystalline form of tenofovir disoproxil base in a water miscible organic solvent and quenching into water saturated with alkali or alkaline earth metal salts, preferably into water saturated with sodium chloride, chilling the saturated aqueous solution to a temperature below 0 to −20° C. preferably below −15° C. more preferably below −10° C. and isolating the crystalline solid from water. The temperature and the saturated solution aid in solidying the solid.

Tenofovir disoproxil Form C of the present invention may be further converted to its fumarate salt.

Figure 1:
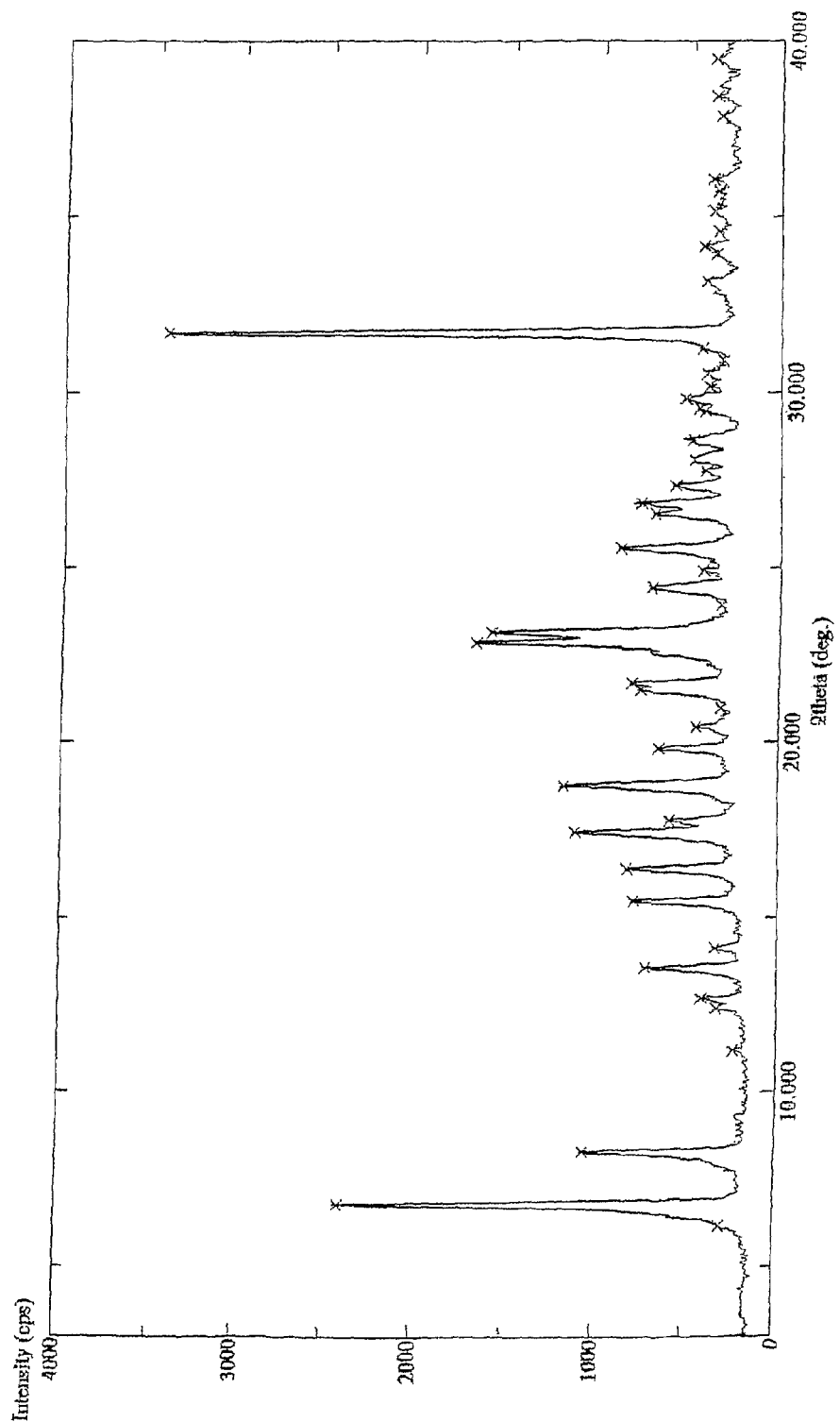
FIG. 1: X-ray diffractogram of crystalline tenofovir disoproxil Form C.

Tenofovir disoproxil Form C of the present invention may be characterized by the X-ray powder diffraction spectrum as shown in FIG. 1, where the vertical axis is intensity and the horizontal axis is the 2θ angle, in degrees.

The XRPD of the tenofovir disoproxil Form C was measured on a Rigaku miniflex advance powder X-ray Powder Diffractometer using a Cu K alpha-1 radiation source.

TABLE 1

| Diffraction angles (2θ°) | Relative Intensity (I/IO) |
| --- | --- |
| 6.19 | 9 |
| 6.79 | 70 |
| 8.28 | 31 |
| 11.15 | 7 |
| 12.38 | 10 |
| 12.66 | 13 |
| 13.54 | 21 |
| 14.13 | 10 |
| 15.47 | 24 |
| 16.39 | 25 |
| 17.40 | 33 |
| 17.74 | 18 |
| 18.72 | 35 |
| 19.82 | 20 |
| 20.44 | 14 |
| 20.99 | 10 |
| 21.49 | 23 |
| 21.71 | 24 |
| 22.87 | 49 |
| 23.17 | 47 |
| 23.97 | 10 |
| 24.44 | 21 |
| 24.91 | 13 |
| 25.53 | 26 |
| 26.51 | 21 |
| 26.8 | 23 |
| 27.31 | 18 |
| 27.7 | 13 |
| 28.09 | 15 |
| 28.65 | 15 |
| 29.47 | 13 |
| 29.55 | 14 |
| 29.82 | 16 |
| 30.17 | 12 |
| 30.53 | 13 |
| 30.89 | 10 |
| 31.23 | 13 |
| 31.67 | 100 |
| 33.16 | 13 |
| 33.94 | 11 |
| 34.15 | 13 |

Tenofovir disoproxil Form C of the present invention may also be characterized by melting point. The melting point preferably ranges from 61 to 66° C. (DSC: onset, open capsule).

EXAMPLES

The invention will be illustrated by the following non-limiting examples.

Example 1

Tenofovir (25 kg) and 1-methyl 2-pyrrolidinone (100 kg) were stirred at 25-30° C. Triethyl amine (25 kg) was added slowly and the reaction mass was heated to 50-55° C. for 30 minutes. Chloromethyl isopropyl carbonate (65 kg) was added to the reaction mass gradually over about 15 to 20 minutes. The reaction mass was then heated to 65-70° C. and stirred for 4 hours and then cooled to 25-30° C.

In another reaction vessel, a saturated solution containing 300 kg sodium chloride, 200 kg of water, and 300 kg crushed ice was stirred to a temperature below −15° C.

The reaction mass from the first step was quenched into the chilled saturated solution maintaining temperature below 0° C. and stirred for 12-15 hours. The resulting solid was filtered and washed with chilled water and spin dried for 1 hour. The solid was further dried in vacuum to obtain 25-30 kg of tenofovir disoproxil Form C.

Example 2

Tenofovir disoproxil (25 kg) was dissolved in isopropyl alcohol (100 liters) at 25-30° C. Fumaric acid (10 kg) was added and the mixture was heated to 50-55° C. for 1 hour, gradually cooled to 25-30° C., further chilled to 10° C. and stirred for 4 hours. The resulting solid was filtered and washed with chilled isopropyl alcohol. The wet cake was stirred in isopropyl acetate (200 ltrs.) at 10-15° C. for 4 hours. The solid was filtered and washed with chilled isopropyl acetate and dried under vacuum to obtain 30 kg of tenofovir disoproxil fumarate.

Example 3

Crude tenofovir disoproxil (5 kg) was dissolved in dimethyl sulfoxide (20 kg), the reaction mass stirred at 25-30° C. and quenched into a reaction vessel containing a saturated solution containing 300 kg sodium chloride, 200 kg of water and 300 kg of crushed ice at a temperature below −15° C. The suspension was stirred for 12-15 hours. The resulting solid was filtered and washed with chilled water and spin dried for 1 hour. The solid was further dried in vacuum to obtain 4.5 kg of pure crystalline tenofovir disoproxil Form C.

Example 4

Crude tenofovir disoproxil (1 kg) was dissolved in methylene dichloride (10 ltrs.) to obtain a clear solution. The clear solution was washed with 1 liter of saturated sodium chloride solution three times. The organic phase was separated and dried by stirring with sodium sulphate and filtered. The solvent was removed by distillation, 10 liters of heptane was added and the resulting slurry was stirred for 30 minutes and filtered to obtain 800 gms of tenofovir disoproxil having monoisoproxil impurity less than 0.2%.

It will be appreciated that the invention may be modified within the scope of the Appended claims.

The invention claimed is:

1. Crystalline Form C of tenofovir disoproxil characterised as having an XRPD pattern comprising peaks at 6.8, 23.2, 25.5 and 31.7°2θ±0.2°2θ.

2. Crystalline Form C of tenofovir disoproxil according to claim 1, characterised in that the XRPD pattern comprises further peaks at 8.3, 17.4, 18.7 and 22.9°2θ±0.2°2θ.

3. Crystalline Form C of tenofovir disoproxil according to claim 1, characterised as having an XRPD pattern as shown in FIG. 1.

4. Crystalline Form C of tenofovir disoproxil according to claim 1, having a melting point ranging from 61°C. to 66°C.

Figure 2:
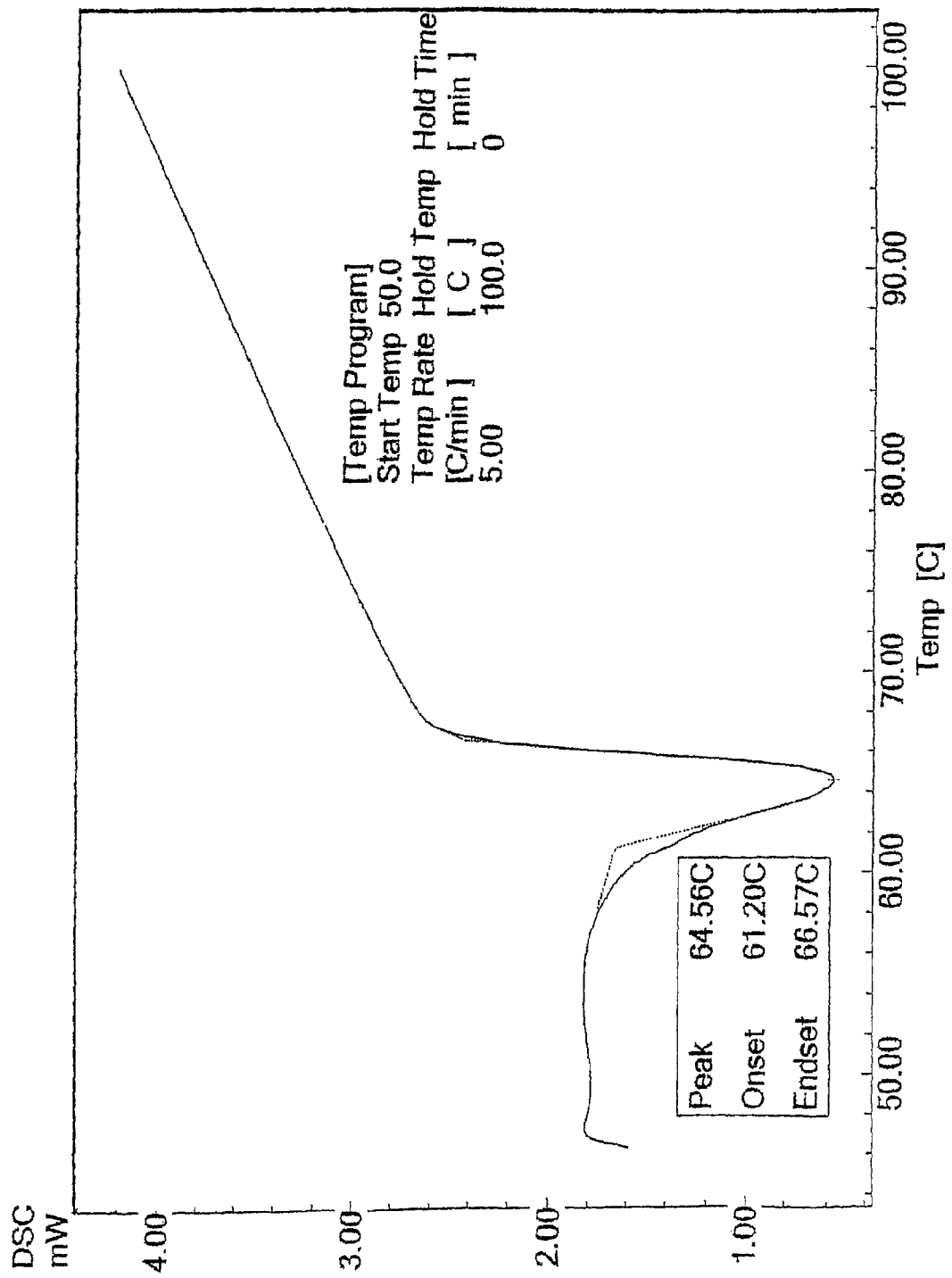
FIG. 2: DSC of crystalline tenofovir disoproxil Form C.

5. Crystalline Form C of tenofovir disoproxil according to claim 1, characterised as having a DSC pattern as shown in FIG. 2.

6. Crystalline Form C of tenofovir disoproxil according to claim 1, containing less than 0.2% tenofovir monoisoproxil.

7. A process for preparing crystalline Form C of tenofovir disoproxil or a salt thereof, the process comprising adding a solution comprising tenofovir disoproxil and an organic solvent to salt-saturated water, cooling the solution to a temperature below 0° C., whereby the crystalline Form C of tenofovir disoproxil having an XRPD pattern comprising peaks at 6.8, 23.2, 25.5 and 31.7°±0.2°precipitates, and optionally converting the crystalline Form C of tenofovir disoproxil to a salt of crystalline Form C of tenofovir disoproxil.

8. The process according to claim 7, wherein the salt-saturated water is water saturated with an alkali or alkaline earth metal salt.

9. The process according to claim 7, wherein the salt-saturated water is water saturated with sodium chloride.

10. The process according to claim 7, wherein the organic solvent is a water miscible organic solvent.

11. The process according to claim 7, wherein the organic solvent is N-methyl pyrrolidone or dimethyl sulfoxide.

12. The process according to claim 7, wherein the aqueous solution comprising the tenofovir disoproxil is cooled to a temperature below −10° C.

13. The process according to claim 7, wherein the crystalline Form C of tenofovir disoproxil is converted to the fumarate salt of crystalline Form C of tenofovir disoproxil.

14. The process according to according to claim 7, wherein the solution of the tenofovir disoproxil in the organic solvent is the reaction mass resulting from a synthesis of the tenofovir disoproxil.

15. The process according to claim 14, wherein the tenofovir disoproxil is synthesised by condensing 9-[2-(R)-(phosphonomethoxy)propyl]adenine with chloromethyl isopropyl carbonate in the organic solvent and in the presence of triethyl amine.

16. The process according to claim 7, wherein the solution of tenofovir disoproxil is prepared by dissolving crude tenofovir disoproxil or any crystalline form of tenofovir disoproxil in the organic solvent.

17. The process according to claim 7, wherein an amount of monoisoproxil impurity in the Form C product is present in an amount less than 1%.

18. The process according to claim 17, wherein the amount of monoisoproxil impurity in the Form C product is present in an amount less than 0.2%.

* * * * *

UNITED STATES PATENT AND TRADEMARK OFFICE
CERTIFICATE OF CORRECTION

| | | |
|---|---|---|
| PATENT NO. | : 8,519,126 B2 | |
| APPLICATION NO. | : 12/989147 | |
| DATED | : August 27, 2013 | |
| INVENTOR(S) | : Manjinder Singh Phull, Rajendra Narayanrao Kankan and Dharmaraj Ramachandra Rao | |

It is certified that error appears in the above-identified patent and that said Letters Patent is hereby corrected as shown below:

In the Claims

Column 8, Line 16, Claim 7, Replace: "31.7°± 0.2°" with --31.7°2θ ± 0.2°2θ--

Signed and Sealed this
Twenty-second Day of October, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,519,126 B2  Page 1 of 1
APPLICATION NO. : 12/989147
DATED : August 27, 2013
INVENTOR(S) : Phull et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 351 days.

Signed and Sealed this
Fifteenth Day of September, 2015

Michelle K. Lee
*Director of the United States Patent and Trademark Office*